United States Patent
Tzoumas et al.

(10) Patent No.: US 10,588,516 B2
(45) Date of Patent: Mar. 17, 2020

(54) DEVICE AND METHOD FOR MULTISPECTRAL OPTOACOUSTIC IMAGING

(71) Applicant: HELMHOLTZ ZENTRUM MUENCHEN DEUTSCHES FORSCHUNGSZENTRUM etc., Neuherberg (DE)

(72) Inventors: Stratis Tzoumas, Munich (DE); Ivan Olefir, Munich (DE); Amir Rozental, Haifa (IL); Vasilis Ntziachristos, Graefelfing (DE)

(73) Assignee: HELMHOLTZ ZENTRUM MUENCHEN DEUTSCHES FORSCHUNGSZENTRUM FUER GESUNDHEIT UND UMWELT (GMBH), Neuherberg (DE)

( * ) Notice: Subject to any disclaimer, the term of this patent is extended or adjusted under 35 U.S.C. 154(b) by 1013 days.

(21) Appl. No.: 15/042,430

(22) Filed: Feb. 12, 2016

(65) Prior Publication Data
US 2016/0235304 A1  Aug. 18, 2016

(30) Foreign Application Priority Data
Feb. 13, 2015 (EP) .................. 15155071

(51) Int. Cl.
*A61B 5/00* (2006.01)
*A61B 5/145* (2006.01)
(Continued)

(52) U.S. Cl.
CPC .......... *A61B 5/0095* (2013.01); *A61B 5/0073* (2013.01); *A61B 5/14542* (2013.01); *G01N 21/1702* (2013.01); *G01N 29/2418* (2013.01); *G01N 2201/067* (2013.01); *G01N 2201/106* (2013.01)

(58) Field of Classification Search
CPC .. A61B 5/0073; A61B 5/0095; A61B 5/14542
See application file for complete search history.

(56) References Cited

U.S. PATENT DOCUMENTS

2011/0306857 A1  12/2011  Razansky et al.

OTHER PUBLICATIONS

Search Report prepared by the European Patent Office dated Aug. 25, 2015, for European Patent Application No. 15155071.2.
(Continued)

*Primary Examiner* — Luther Behringer
*Assistant Examiner* — Sean D Mattson
(74) *Attorney, Agent, or Firm* — Sheridan Ross P.C.

(57) ABSTRACT

A device and an according method for multispectral optoacoustic imaging of an object is provided comprising: an irradiation unit configured to irradiate the object with electromagnetic radiation at two or more different irradiation wavelengths the electromagnetic radiation having a time-varying intensity; a detection unit configured to detect acoustic waves generated in the object upon irradiating the object with the electromagnetic radiation at the different irradiation wavelengths; and a processing unit configured to reconstruct images of the object based on the detected acoustic waves generated in the object at each of the irradiation wavelengths and to determine a spatial distribution of at least one first concentration value, which relates to a concentration of at least one electromagnetic radiation absorber in the object.

11 Claims, 5 Drawing Sheets

Figure 1:
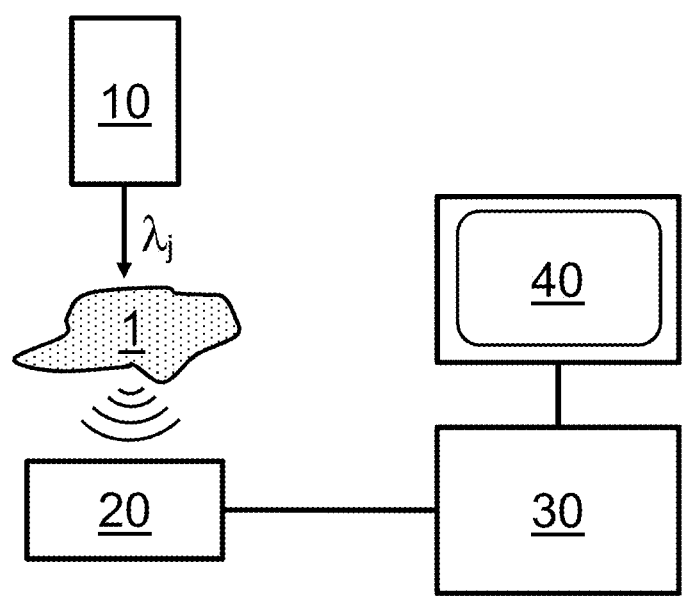

(51) Int. Cl.
    G01N 29/24    (2006.01)
    G01N 21/17    (2006.01)

(56)  References Cited

OTHER PUBLICATIONS

Alles Erwin J., et al.: "In vivo photoacoustic oxygen saturation imaging without the need for fluence estimate"; 2014 IEEE International Ultrasonics Symposium Proceedings, Sep. 3, 2014, pp. 1284-1287.
Ben Cox, et al.: "Quantitative spectroscopic photoacoustic imaging: a review"; Journal of Biomedical Optics, vol. 17, No. 6, p. 061202 (Jun. 2012).
Pulkkinen A., et al.: "A Bayesian approach to spectral quantitative photoacoustic tomography"; Inverse Problems, vol. 30, No. 6, May 30, 2014, p. 65012.

DEVICE AND METHOD FOR MULTISPECTRAL OPTOACOUSTIC IMAGING

CROSS REFERENCE TO RELATED APPLICATIONS

This application claims the benefit of European Patent Application No. 15155071.2 filed Feb. 13, 2015, the disclosures of which is incorporated by reference herein.

The present invention relates to a device and a method for multispectral optoacoustic imaging, in particular for determining a quantitative image relating to concentrations of one or more chromophores in an object, according to the independent claims.

Optoacoustic imaging is based on the photoacoustic effect, according to which ultrasonic waves are generated due to absorption of electromagnetic radiation by an object, e.g. a biological tissue, and a subsequent thermoelastic expansion of the object. Excitation radiation, for example laser light or radiofrequency radiation, can be pulsed radiation with short pulse durations or continuous radiation with varying amplitude or frequency.

An important advancement in optoacoustics is imaging of different moieties by resolving their distinct absorption spectra. This is typically achieved by illuminating the object imaged at multiple wavelengths and performing spectral unmixing operations in the collected data. Imaging of such moieties is important to different applications.

In biological and medical applications for example, tissue blood oxygenation is a significant metric that can infer valuable knowledge regarding tissue viability, metabolism, hypoxia and neuronal activation. Few imaging modalities can provide quantitative information of deep tissue blood oxygenation in high spatial and temporal resolution. By utilizing several excitation wavelengths so-called multispectral optoacoustic images (also referred to as spectroscopic optoacoustic images) of high spatial and temporal resolution can be obtained, that are related to tissue optical absorption, which can be used to infer blood oxygenation. However, accurate quantification of a spatial distribution of chromophores, like oxygenated and deoxygenated hemoglobin, in deep tissue by means of multispectral optoacoustic tomography (MSOT) remains a challenge, in particular at depths exceeding 3 mm.

Optoacoustic images are proportional to the absorbed energy density $H(r,\lambda)$ (where r denotes the position and $\lambda$ denotes the wavelength of the excitation source), which depends on the spatial distribution of the optical absorption coefficient $\mu_a(r,\lambda)$ of tissue and the optical fluence $\Phi(r,\lambda)$, i.e. $H(r,\lambda) = \mu_a(r,\lambda) \Phi(r,\lambda)$. Assuming $\mu_a(r,\lambda)$ known, the concentrations of tissue absorbers can be estimated in each position r using linear spectral unmixing methods. Thus valuable physiological (e.g. blood oxygenation in tissue) and molecular information (e.g. spatial localization and concentration estimation of molecular probes) can be extracted. However, the $\mu_a(r,\lambda)$ distribution is not explicitly known from raw optoacoustic images, since the information obtained is coupled to the unknown optical fluence $\Phi(r,\lambda)$. Decomposing the absorbed energy density $H(r,\lambda)$ into the optical fluence $\Phi(r,\lambda)$ and the optical absorption component $\mu_a(r,\lambda)$ is a major challenge in the MSOT problem.

A possible formulation for solving the problem of quantitative optoacoustic imaging (also referred to as a quantitative photoacoustic tomography, or qPAT) is a model-based optical property estimation approach. Under this formulation, the optical fluence $\Phi(r,\lambda; \mu_a(r,\lambda), \mu_s(r,\lambda))$ is related to the spatial distribution of the optical absorption $\mu_a(r,\lambda)$ and scattering $\mu_s(r,\lambda)$ coefficients of the tissue imaged, using a light propagation model. A number of non-linear model-based inversion methods have been published that seek to simultaneously extract the optical fluence and tissue optical properties (absorption and scattering coefficients), given the absorbed energy density $H(r,\lambda)$ at a single or multiple wavelengths by minimizing the functional $\|H(r,\lambda) - \Phi(r,\lambda; \mu_a(r,\lambda), \mu_s(r,\lambda)) \mu_a(r,\lambda)\|$. Optical property estimation methods may operate in the signal or the image domain, they may operate under one excitation wavelength (where optical scattering needs to be known for achieving uniqueness) or under multiple excitation wavelengths and they may also be combined with a model for acoustic propagation. Their common characteristic is that they seek to minimize the functional $\|H(r,\lambda) - \Phi(r,\lambda; \mu_a(r,\lambda), \mu_s(r,\lambda)) \mu_a(r,\lambda)\|$ for obtaining quantitative values of tissue absorption coefficients.

A major disadvantage of the optical property estimation approach is that it typically depends on the accurate estimation of the absorbed energy density $H(r,\lambda)$ in the whole illuminated tissue volume. Typically, optoacoustic images $P(r,\lambda)$ are proportional to the absorbed energy density $H(r,\lambda)$ and to a space dependent scaling factor $C(r)$, i.e. $P(r,\lambda) = C(r)H(r,\lambda)$, where $C(r)$ depends on the spatial impulse response of the system and the (generally unknown) spatially varying Grüneisen coefficient. Thus, the estimation of $H(r,\lambda)$ from optoacoustic images may be prone to error due to scaling effects typically not included in tomographic reconstruction (such as the spatial impulse response of the system or ultrasound attenuation) or uncertainties in estimating the Grüneisen coefficient of different tissue types. Moreover, if the absorbed energy density is unknown or significantly wrong in one part of the illuminated volume (common in the case of limited view systems or under ultrasound scattering incidents) the inversion process may be compromised. Finally, optical property estimation approaches define large scale inverse problems with thousands of unknown parameters, which result in high computational complexity. For these reasons the application of such methodologies in the case of experimental tissue measurements of complex structure, such as biological tissues, is so far limited.

It is an object of the invention to provide a device and method for multispectral optoacoustic imaging allowing for an improved quantification of a spatial distribution of at least one value relating to the concentration of one or more chromophores in an object.

This object is achieved by the device and the method according to the independent claims.

The device for multispectral optoacoustic imaging of an object according to the invention comprises: an irradiation unit configured to irradiate the object with electromagnetic radiation at two or more different irradiation wavelengths, said electromagnetic radiation having a time-varying intensity; a detection unit configured to detect acoustic waves generated in the object upon irradiating the object with the electromagnetic radiation at the different irradiation wavelengths; a processing unit configured to reconstruct images of the object based on the detected acoustic waves generated in the object at each of the irradiation wavelengths and to determine a spatial distribution of at least one first concentration value, which relates to a concentration of at least one electromagnetic radiation absorber in the object, wherein the determination of the spatial distribution of the at least one first concentration value is based on the reconstructed images at the different irradiation wavelengths, on at least one wavelength-dependent extinction coefficient of the at least one electromagnetic radiation absorber in the object, and on a linear combination of at least two model spectra, the model spectra representing wavelength-dependent basis functions of a radiation fluence or of a function of a radiation fluence in the object. Preferably, the radiation fluence is a normalized radiation fluence and/or the model spectra represent the normalized wavelength dependence of the radiation fluence.

The method for multispectral optoacoustic imaging of an object according to the invention comprises the following steps: irradiating the object with electromagnetic radiation at two or more different irradiation wavelengths, said electromagnetic radiation having a time-varying intensity; detecting acoustic waves generated in the object upon irradiating the object with the electromagnetic radiation at the different irradiation wavelengths; reconstructing images of the object based on the detected acoustic waves generated in the object at each of the irradiation wavelengths and determining a spatial distribution of at least one first concentration value, which relates to a concentration of at least one electromagnetic radiation absorber in the object, wherein the determination of the spatial distribution of the at least one first concentration value is based on the reconstructed images at the different irradiation wavelengths, on at least one wavelength-dependent extinction coefficient of the at least one electromagnetic radiation absorber in the object, and on a linear combination of at least two model spectra, the model spectra representing wavelength-dependent basis functions of a radiation fluence or of a function of a radiation fluence in the object. Preferably, the radiation fluence is a normalized radiation fluence and/or the model spectra represent the normalized wavelength dependence of the radiation fluence.

The invention is based on the approach to determine a quantitative image, in particular a spatial distribution of a relative concentration, of at least one radiation absorber in the object considering i) two or more optoacoustic images, which are reconstructed from acoustic waves emanating from the object upon irradiating the object with transient electromagnetic radiation at two or more different irradiation wavelengths, and ii) a linear combination of at least two wavelength-dependent model spectra that correspond to basis functions of a, preferably normalized, wavelength-dependent radiation fluence within the object. Within the meaning of the invention a basis function preferably corresponds to an element of a particular basis for a specific function space, whereby a linear combination of basis functions can represent every continuous function in the specific function space (in analogy to the fact that every vector in a vector space can be represented as a linear combination of basis vectors). Accordingly, in the context of the invention, the term "model spectrum" and "basis function" is also referred to as fluence Eigenspectrum or Eigenspectrum.

According to the inventive approach, instead of using a model-based optical property estimation approach in which a model of light propagation in the object is used in order to extract radiation fluence as well as absorption coefficients from images of an estimated absorbed energy density in the object, a linear combination of a set of wavelength-dependent model spectra is used, wherein the linear combination is obtained by multiplying each model spectrum of the set of model spectra by a wavelength-independent parameter and adding the results. Preferably, the model spectra of a set of model spectra are determined in advance, e.g. by means of simulation of and/or measurement on a representative medium containing the at least one radiation absorber, and are characteristic for the at least one radiation absorber.

By means of the invention the following advantages, in particular over optical property estimation approaches, are achieved: (i) A small-scale optimization problem with much smaller dimensionality can be defined. (ii) Application in a per-pixel basis is possible, meaning that full and accurate image reconstruction of the whole illuminated volume is not an absolute prerequisite. (iii) The application can be performed in a selected part of the whole image, whereby the convergence in an accurately reconstructed area is not affected by possibly corrupted information in different parts of the image. (iv) The approach according to the invention relies on relative values of the absorbed energy density (i.e. the wavelength dependence of the absorbed energy density: $H(r,\lambda)/\|H(r)\|$, whereby $\|H(r)\|$ corresponds to the norm of the absorbed energy density across all wavelengths at a position r) rather than absolute values of the absorbed energy density $H(r,\lambda)$, avoiding further complications like the need for perfect system calibration or estimating the Grüneisen coefficient of tissue, i.e. parameters which have been shown to affect the performance of model-based optical property estimation approaches.

As a result, the invention allows for exact and reliable quantification of a spatial distribution of at least one value relating to the concentration of one or more chromophores in an object, in particular also in tissue depths exceeding 3 mm.

In general, the invention relates to a device and a method for quantifying the distribution of one or more chromophores inside media that attenuate light using optoacoustic measurements. Although the invention is particularly suited for quantifying tissue oxygenation, in particular blood oxygen saturation $sO_2$, it can advantageously also be used in resolving and/or quantifying the relative concentration of any light absorber distribution inside any medium containing at least one light absorber.

According to a preferred embodiment, the processing unit is configured to determine spatial distributions of at least two first concentration values relating to concentrations of at least two electromagnetic radiation absorbers, for example $HbO_2$ and HHb, in the object, wherein the determination of the spatial distributions of the at least two first concentration values is based on the reconstructed images at the different irradiation wavelengths, on the at least two wavelength-dependent extinction coefficients of the at least two chromophores, for example $HbO_2$ and HHb, present in the object, and a linear combination of the at least two model spectra, and to derive a spatial distribution of a second concentration value, in particular a relative concentration value like $sO_2$, from the determined spatial distributions of the at least two first concentration values.

According to yet another preferred embodiment, the at least two model spectra correspond to a minimized number of model spectra, which have been determined for the at least one electromagnetic radiation absorber, e.g. $HbO_2$ and HHb, assumed to be in the object. Preferably, the minimized number of model spectra is between 3 and 8, in particular between 3 and 5.

Moreover, it is preferred that the at least two wavelength-dependent model spectra have been determined by determining a set of spectral patterns for different depths in a medium and for different concentrations of the at least one electromagnetic radiation absorber in the medium, and by applying a statistical procedure on the set of spectral patterns.

Preferably, the set of spectral patterns having been obtained from analytical solutions or from numerical solutions of the diffusion equation or the radiative transfer equation for different wavelengths and/or from Monte Carlo simulations of light propagation for different wavelengths and/or from a set of experimental measurements for different wavelengths.

Preferably, the statistical procedure applied on the set of spectral patterns comprises a principal component analysis (PCA) and/or a kernel principal component analysis (kernel PCA) and/or a linear discriminant analysis (LDA).

According to another preferred embodiment, the linear combination of the model spectra corresponds to an addition of a mean model spectrum $\Phi_M(\lambda)$ and a linear combination of a first number p of further model spectra $\Phi_i(\lambda)$, wherein each of the further model spectra $\Phi_i(\lambda)$ is multiplied by a model parameter $m_i$: $\Phi_M(\lambda) + \Sigma^p_{i=1} m_i \Phi_i(\lambda)$.

Preferably, the irradiation unit being configured to irradiate the object with electromagnetic radiation at a second number w of different irradiation wavelengths, wherein the second number w is larger than or equal to the sum of the first number p of further model spectra and a number $n_c$ of the first concentration values to be determined: $w \geq p + n_c$.

It is, moreover, preferred that the determination of the spatial distribution of two first concentration values $c'_1(r)$ and $c'_2(r)$, which relate to concentrations of two different electromagnetic radiation absorbers in the object, comprises an inversion of a system of non-linear equations, wherein the inversion of the system of non-linear equations is performed simultaneously for a selected set of different positions r distributed in the image domain.

It is further preferred that the determination of the spatial distribution of two first concentration values $c'_1(r)$ and $c'_2(r)$, which relate to concentrations of two different electromagnetic radiation absorbers in the object at a position r, comprises an inversion of a system of non-linear equations given by $$P(r,\lambda_j) = (\Phi_M(\lambda_j) + \Sigma^p_{i=1} m_i^r \Phi_i(\lambda_j))(c'_1(r)\varepsilon_1(\lambda_j) + c'_2(r)\varepsilon_2(\lambda_j)), \text{ with } j = 1 \ldots w,$$

$P(r, \lambda_j)$ denoting the reconstructed image intensity of the object at an irradiation wavelength $\lambda_j$ and position r, $\Phi_M(\lambda_j) + \Sigma^p_{i=1} m_i^r \Phi_i(\lambda_j)$ denoting a linear combination of the wavelength-dependent model spectra $\Phi_M(\lambda_j)$ and $\Phi_i(\lambda_j)$, with $i = 1 \ldots p$, at an irradiation wavelength $\lambda_j$ and position r, wherein $m_i^r$ denotes the values of the model parameters at a position r, and $c'_1(r)\varepsilon_1(\lambda_j) + c'_2(r)\varepsilon_2(\lambda_j)$ denotes a linear combination of electromagnetic radiation extinction coefficients $\varepsilon_1(\lambda_j)$ and $\varepsilon_2(\lambda_j)$ of the two electromagnetic radiation absorbers at an irradiation wavelength $\lambda_j$, wherein $c'_1(r)$ and $c'_2(r)$ denote the two first concentration values at a position r.

According to yet another preferred aspect of the invention, the inversion of the system of non-linear equations is performed simultaneously for a number $N_{grid}$ of different positions $r_n$, with $n = 1 \ldots N_{grid}$, corresponding to a grid in the image, and the variation of one or more of the model parameters between neighbor positions is constrained.

Preferably, the system of non-linear equations is solved through the minimization of the difference between the reconstructed image intensity and the model (i.e. $\Sigma_j \| P(r, \lambda_j) - (\Phi_M(\lambda_j) + \Sigma^p_{i=1} m_i^r \Phi_i(\lambda_j))(c'_1(r)\varepsilon_1(\lambda_j) + c'_2(r)\varepsilon_2(\lambda_j)) \|_{nrm1}^{pwr1}$, where nrm1 denotes an appropriate norm and pwr1 an appropriate power) at multiple positions corresponding to a grid in the image, and the simultaneous minimization of the variation of model parameters between neighbor grid points. Preferably, this is achieved, e.g., through the minimization of a cost function $f_{grid}$ that is a linear combination of the difference between the reconstructed image intensity and the model at multiple positions corresponding to a grid in the image (i.e. $\Sigma_n \Sigma_j \| P(r_n, \lambda_j) - (\Phi_M(\lambda \cdot j) + \Sigma^p_{i=1} m_i^{r(n)} \Phi_i(\lambda_j))(c'_1(r_n)\varepsilon_1(\lambda_j) + c'_2(r_n)\varepsilon_2(\lambda_j)) \|_{nrm1}^{pwr1}$) and the simultaneous minimization of the variation of model parameters corresponding to neighbor positions in the image (i.e. $\| m_i^{r(n1)} - m_i^{r(n2)} \|_{nrm2}^{pwr2}$ where $r_{n1}$ and $r_{n2}$ correspond to two neighbor positions in the grid and nrm2 denotes an appropriate norm and pwr2 an appropriate power). Preferably, the minimization function $f_{grid}$ would take the following form: $f_{grid} = \Sigma_n \Sigma_j \| P(r_n, \lambda_j) - (\Phi_M(\lambda_j) + \Sigma^p_{i=1} m_i^{r(n)} \Phi_i(\lambda_j))(c'_1(r_n)\varepsilon_1(\lambda_j) + c'_2(r_n)\varepsilon_2(\lambda_j)) \|_{nrm1}^{pwr1} + \Sigma_{n,m} \lambda_{n,m} \| m_i^{r(n)} - m_i^{r(m)} \|_{nrm2}^{pwr2}$ where $\lambda_{n,m}$ are appropriate weight coefficients.

It is, moreover, preferred that in the inversion of the system of non-linear equations the values of the model parameters $m_i^r$ are constrained to lie within a limited region (i.e. $\lim^{min}_i < m_i^r < \lim^{max}_i$, where the values $\lim^{min}_i$ and $\lim^{max}_i$ are defined through simulations or experimental measurements), and/or that the difference between the unknown values $m_i^r$ and some predefined values $\hat{m}_i^r$ is also minimized along with the minimization of the cost function $f_{grid}$. Preferably, this is performed through the minimization of a second cost function $g_{grid}$ that constitutes a linear combination of $f_{grid}$ and a weighted difference between the model parameters $m_i^r$ and the predefined values $\hat{m}_i^r$ (also referred to as priors), i.e. $g_{grid} = f_{grid} + w_i^r \| m_i^r - \hat{m}_i^r \|_{nrm3}^{pwr3}$, where nrm3 denotes an appropriate norm, pwr3 an appropriate power and $w_i^r$ an appropriate weight coefficient. Preferably, the priors $\hat{m}_i^r$ are obtained through simulations or experimental measurements.

Figure 2:
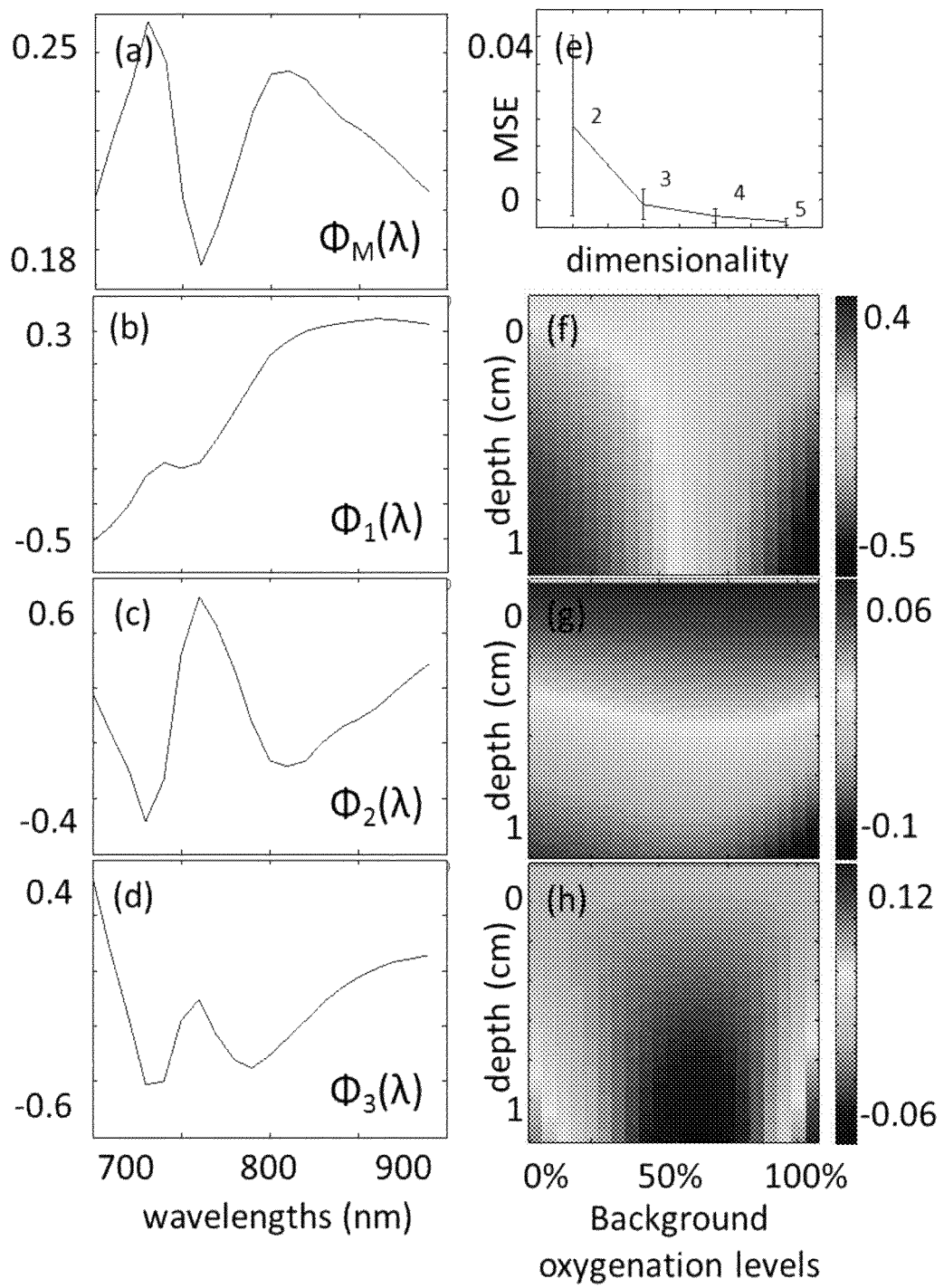
Figure 3:
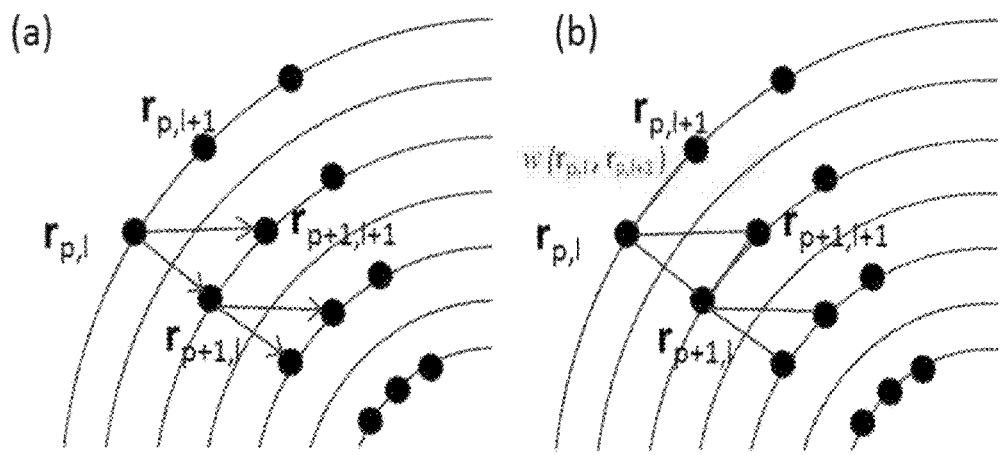
Figure 4:
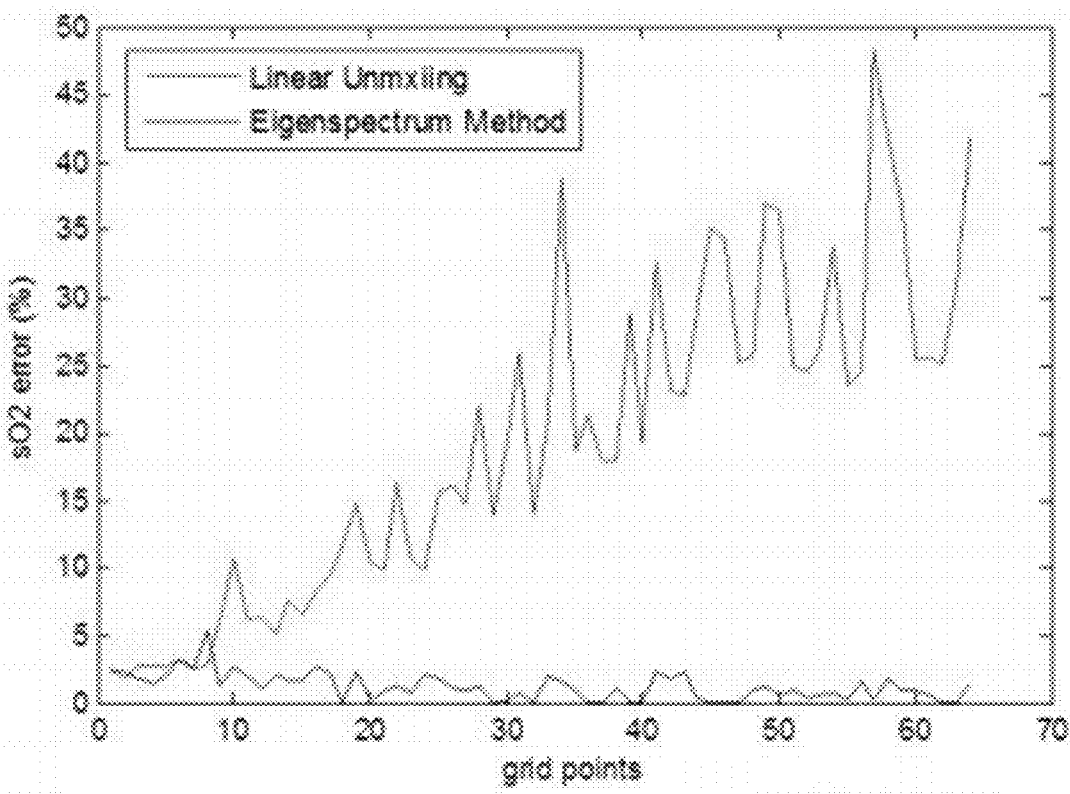

The above and other elements, features, characteristics and advantages of the present invention will become more apparent from the following detailed description of preferred embodiments with reference to the attached figures showing:

FIG. 1 an example of a device for multispectral optoacoustic imaging;

FIG. 2 an example of an Eigenspectrum model of wavelength-dependent optical fluence: (a-d) Model spectra $\Phi_M(\lambda)$, $\Phi_1(\lambda)$, $\Phi_2(\lambda)$ and $\Phi_3(\lambda)$ at utilized wavelengths $\lambda$. (e) Mean Square Error (MSE) of the model on a training dataset for different model dimensionalities. (f-h) Values of parameters $m_1$, $m_2$ and $m_3$ on the training dataset as a function of depth (y axis) and tissue oxygenation (x axis);

FIG. 3 an example of an incorporation of constraints on the spatial characteristics of fluence parameters $m_1$, $m_2$ and $m_3$ in the case of simultaneous inversion on a grid of points. (a) A directed graph on the grid of points enforces a constraint on the values of $m_2$ model parameter with depth. (b) A non-directed graph on the grid of points penalizes great variations of the fluence parameters between neighbor points;

FIG. 4 an example of an $sO_2$ estimation error for all grid points using the Eigenspectrum method with simultaneous inversion on a grid of points and a non-negatively constrained linear unmixing approach.

Figure 5:
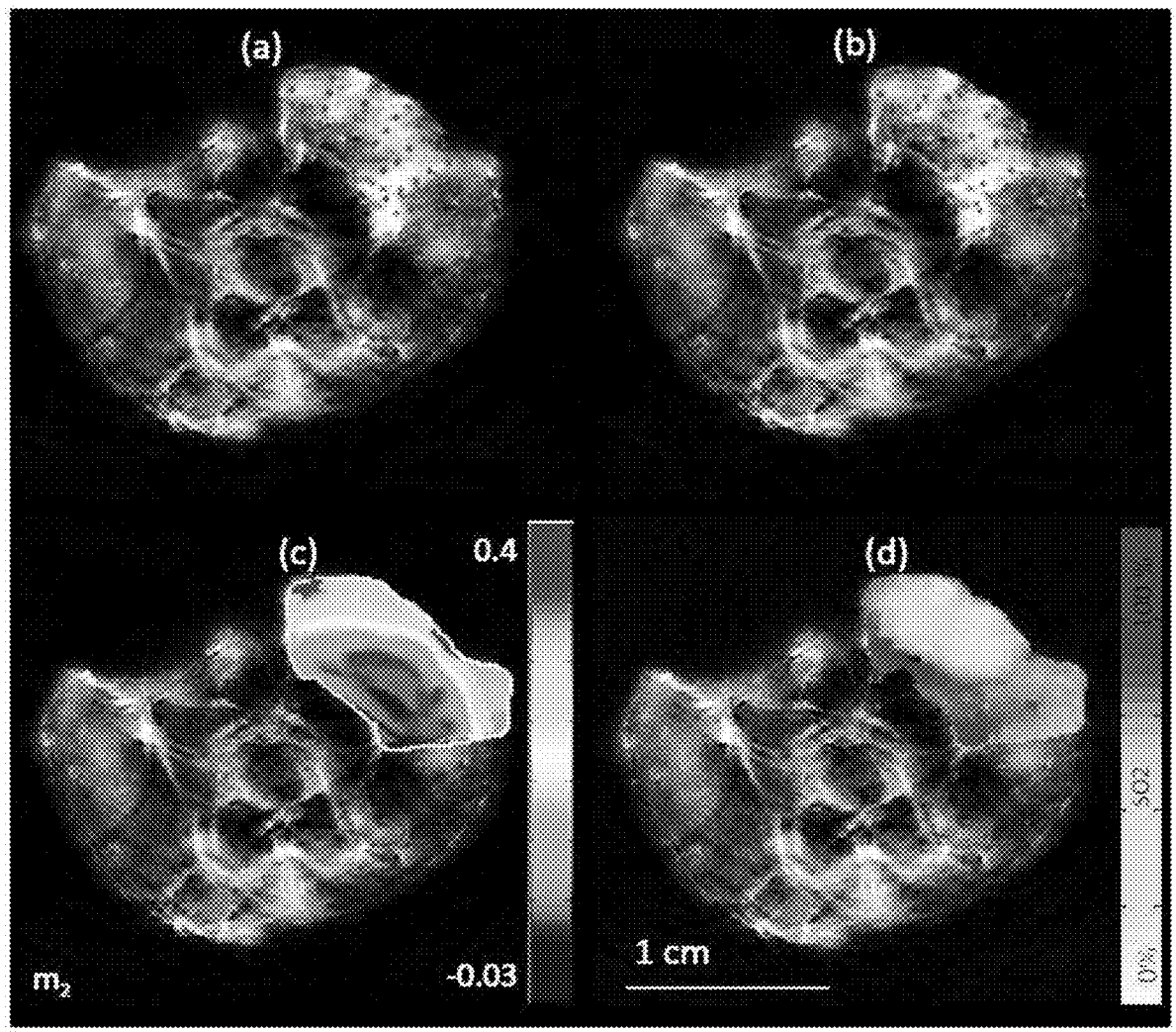

FIG. 5 (a) an MSOT image (one wavelength presented) of a tumor-bearing nude mouse, wherein the points in the image correspond to the initial grid selected for inversion. (b) Automatic refinement of the initial grid for maximizing the SNR in the pixels used for inversion. (c) Map of fluence parameter $m_2$ in the convex hull of the inversion grid. (d) Estimation of tissue blood $sO_2$ after fluence correction; and FIG. 6 a schematic overview on an example of processes and algorithms of a method for multispectral optoacoustic imaging.

FIG. 1 shows an example of a device for multispectral optoacoustic imaging comprising an irradiation unit 10 which is configured to irradiate an object 1 with electromagnetic radiation at two or more different irradiation wavelengths $\lambda_j$ and a time-varying intensity.

For example, the irradiation unit 10 may comprise at least one laser source which is configured to emit visible and/or near-infrared light, for example between 690 nm and 900 nm, preferably at 5 to 20 excitation wavelengths. Preferably, the emitted light is pulsed and/or amplitude- or frequency-modulated.

By irradiating the object 1 with transient, in particular pulsed and/or modulated, electromagnetic radiation, acoustic waves are generated, which are detected by detection unit 20, which comprises one or more ultrasound detectors, e.g. one or more piezoelectric detectors. Preferably, the detection unit 20 comprises a two-dimensional or three-dimensional array of ultrasound detector elements by which the acoustic waves generated in the object 1 can be detected and spatially resolved.

The object 1 can preferably be a biological tissue, like a part of a human or animal body. Depending on the particularities of the desired application, pre-clinical or clinical applications, a holder (not shown) can be provided for holding and positioning the object 1, e.g. a tissue sample or a small animal, relative to the irradiation unit 10 and the detection unit 20. Alternatively or additionally, the irradiation unit 10 and detection unit 20 can be integrated in a handheld device which can be manually placed onto the object 1 and/or moved relative to the object 1.

In the detector unit 20 the detected acoustic waves are converted into corresponding detector signals which are forwarded to processing unit 30 which is configured to reconstruct images of the object 1 based on the detector signals that are obtained at each of the irradiation wavelengths $\lambda_j$.

The processing unit 30 is further configured to determine a spatial distribution of a relative concentration of at least one radiation absorber contained in the object 1 by considering the reconstructed images of the object 1 at different irradiation wavelengths $\lambda_j$ and the radiation fluence or a function of the radiation fluence in the object 1, e.g. the normalized radiation fluence, wherein the radiation fluence or the function of the radiation fluence is based on a linear model of the radiation fluence. According to the linear radiation fluence model, at least two model spectra representing wavelength-dependent basis functions of the radiation fluence or a function thereof are linearly combined.

Preferably, a display unit 40, e.g. a computer monitor, is provided for displaying the reconstructed images and/or the determined spatial distribution of the relative concentration of the at least one radiation absorber contained in the object 1.

In the following, preferred aspects of determining a spatial distribution of the relative concentration of the at least one radiation absorber contained in the object 1 will be elucidated in detail.

An algorithmic solution for obtaining quantitative measures of blood oxygenation from multispectral optoacoustic images based on a new formulation of the quantification problem as a per-pixel non-linear spectral unmixing problem will be elucidated in more detail in section "PROBLEM FORMULATION" below.

Preferably, a simple linear model of wavelength-dependent basis functions is created for capturing the spectral perturbations of the optical fluence in tissue using training data, which will be elucidated in more detail in section "THE EIGENSPECTRUM MODEL OF OPTICAL FLUENCE" below.

Preferably, based on this model, a non-linear inversion scheme is formulated for obtaining quantitative blood $sO_2$ estimates from MSOT images, which will be elucidated in section "INVERSION" below. The proposed inversion scheme further exploits prior knowledge on structural and spectral characteristics of the optical fluence for enhancing inversion accuracy.

Finally the application of the novel algorithmic solution on in vivo multispectral optoacoustic images will be demonstrated in section "APPLICATION ON TISSUE IMAGES" below.

Problem Formulation

Optical Fluence and Acquiring Accurate $sO_2$ Estimates

With oxygenated ($HbO_2$) and deoxygenated (HHb) hemoglobin being the main tissue absorbers, optoacoustic images of tissues $P(r,\lambda)$ can be related to the concentrations of $HbO_2$ and HHb through a non-linear relation, i.e.

$$P(r, \lambda) = C(r) \|\Phi(r)\|_2 \frac{\Phi(r, \lambda)}{\|\Phi(r)\|_2} \cdot (c_{HbO2}(r) \cdot \varepsilon_{HbO2}(\lambda) + c_{HHb}(r) \cdot \varepsilon_{HHb}(\lambda)). \quad (1)$$

In Eq. (1), C(r) is a space dependent scaling factor that includes the effect of the Grüneisen coefficient ($\Gamma(r)$) and possibly additional physical phenomena (e.g. ultrasound attenuation) and system effects (e.g. the space and frequency dependent sensitivity of the ultrasound sensors). $\varepsilon_{HbO2}(\lambda)$ and $\varepsilon_{HHb}(\lambda)$ are the wavelength dependent molar extinction coefficients of hemoglobin, while $c_{HbO2}(r)$ and $c_{HHb}(r)$ are the associated concentrations at a position r. $\|\Phi(r)\|_2$ is the norm of the optical fluence across all wavelengths at a position r, while $\Phi(r,\lambda)/\|\Phi(r)\|_2$ is the normalized wavelength dependence of optical fluence at a specific position, a term that will also be referred to as $\Phi'(r,\lambda)$ in connection with the present invention.

The space-only dependent factors C(r) and $\|\Phi(r)\|_2$ do not affect the estimation of $sO_2$ (Eq. (2)) which is calculated as a ratio once the relative concentrations of $HbO_2$ and HHb are known ($c'_{HbO2}(r)$=Const(r)·$c_{HbO2}(r)$ and $c'_{HHb}(r)$=Const(r)·$c_{HHb}(r)$, respectively).

$$sO_2(r) = \frac{c'_{HbO2}(r)}{c'_{HbO2}(r) + c'_{HHb}(r)}. \quad (2)$$

An estimate of the wavelength dependence of the optical fluence $\Phi'(r,\lambda)$ is required for accurately extracting the relative values of $c'_{HbO2}(r)$ and $c'_{HHb}(r)$. However, $\Phi'(r,\lambda)$ is in general an unknown function.

According to a preferred aspect of the invention, the wavelength dependence of optical fluence $\Phi'(r,\lambda)$ is not an arbitrary function of wavelength, but it is assumed to only lie within a limited subspace of spectral patterns within tissue. This aspect is based on the notion that the spectrum of optical fluence is a result of the cumulative light absorption by certain tissue absorbers, so the spectrum of optical fluence will always be related to the spectra of these absorbers through a complex relation.

According to another preferred aspect, it is assumed that this subspace of spectral patterns can be accurately described using a low-dimensional linear model. In the section "THE EIGENSPECTRUM MODEL OF OPTICAL FLUENCE" the creation of such a model that consists of a linear combination of a small number of characteristic tissue optical fluence spectra, also referred to as Eigenspectra, will be described in detail.

Non-linear Spectral Unmixing Formulation

According to yet another aspect, it is assumed that it is possible to define a linear model that is based on a superposition of a mean spectrum $\Phi_M(\lambda)$ and a number of optical fluence Eigenspectra $\Phi_i(\lambda)$ to accurately characterize $\Phi'(r,\lambda)$ at each arbitrary position r within tissue, then the non-linear mixture model for MSOT images at a position r can be written as:

$$P(r, \lambda) = \left(\Phi_M(\lambda) + \sum_{i=1}^{P} m_i^r \Phi_i(\lambda)\right). \quad (3)$$

$$(c'_{HbO2}(r) \cdot \varepsilon_{HbO2}(\lambda) + c'_{HHb}(r) \cdot \varepsilon_{HHb}(\lambda)).$$

The solution for the P+2 unknowns (namely the P model parameters, $m_{1...P}^r$ and the relative blood concentrations $c'_{HbO2}(r)$ and $c'_{HHb}(r)$) can then be given using an appropriate non-linear inversion approach and at least P+2 excitation wavelengths. As stated before, the relative blood concentrations $c'_{HbO2}(r)$ and $c'_{HHb}(r)$ are proportional to the originals $c_{HbO2}(r)$ and $c_{HHb}(r)$ with regard to a scaling factor, however this fact does not affect the computation of $sO_2$, which is a ratiometric (relative) measurement.

In order to achieve the aforementioned non-linear spectral un-mixing formulation, a linear model for the optical fluence, in the form of $(\Phi_M(\lambda), \Phi_1(\lambda), \ldots, \Phi_P(\lambda))$ is established. The model is able to accurately describe the wavelength dependence of the optical fluence $\Phi'(r,\lambda)$, at any arbitrary position within tissue and independently of the surrounding optical properties and $sO_2$ values.

The Eigenspectrum Model of Optical Fluence

The wavelength-dependent optical fluence in tissue may take a number of different spectral patterns. The variation of optical fluence per wavelength is not random but follows a pattern typically determined by tissue depth, tissue scattering, blood $sO_2$ values and overall blood concentration. Preferably, by using Principal Component Analysis (PCA) on a set of different optical fluence spectral patterns, also referred to as training set, a linear model $(\Phi_M(\lambda), \Phi_1(\lambda), \ldots, \Phi_P(\lambda))$ consisting of a small number of fluence Eigenspectra $\Phi_i(\lambda)$ is determined. PCA is used for offering a minimum square error property in capturing the spectral variability of the optical fluence spectral patterns of the training set in a linear manner.

By testing the Eigenspectrum model in a set of optical fluence spectral patterns produced in completely heterogeneous media with greatly varying and randomly distributed optical properties and oxygenation values, it was found that the Eigenspectrum model can accurately capture all such optical fluence spectral patterns with a very small mean square error (<2%), and it was confirmed that, independent of such conditions (i.e. optical property variation), the spectral patterns of optical fluence lie in a confined spectral subspace that can be accurately modeled by the Eigenspectrum model.

In the following subsections, the light propagation models that are hereby used as well as an analytical description of the procedure for creating the Eigenspectrum model from training data are elucidated in detail.

Light Propagation Models

Preferably, a light propagation model based on the diffusion equation is employed, wherein the wavelength dependent optical fluence model $(\Phi_M(\lambda), \Phi_1(\lambda), \ldots, \Phi_P(\lambda))$ is created using the solution of the diffusion equation for infinite homogeneous media, i.e., $$\Phi_z = \Phi_0 \exp(-\mu_{eff} z), \quad (4)$$

where z denotes a distance from the source (tissue depth) and $\mu_{eff}$ is the effective attenuation coefficient: $\mu_{eff} = \sqrt{3\mu_\alpha(\mu_\alpha+\mu_s')}$, $\mu_s'$ being the reduced scattering coefficient and $\mu_\alpha$ the absorption coefficient.

Alternatively, a finite element solution of the diffusion approximation for arbitrary structure of optical properties may be used.

The Eigenspectrum Model

Preferably, for producing a training dataset to generate the optical fluence Eigenspectrum model, simulations based on the analytical solution of the diffusion equation (Eq. (4)) are performed.

For example, a number of optical fluence spectral patterns $\Phi_{z,ox}(\lambda)$ are computed for wavelengths $\lambda=700$ nm to 890 nm with a step size of 10 nm, for depths from $z=0$ cm to $z=1$ cm with a step size of 0.143 mm, and for uniform hemoglobin distribution at a constant oxygenation, varying from ox=0% to ox=100% with a step of 5%. Constant optical properties of $\mu_\alpha=0.3$ cm$^{-1}$ (at the isosbestic point of hemoglobin at 800 nm) and $\mu_s'=10$ cm$^{-1}$ (constant for all wavelengths) are used. The so computed 70×21 optical fluence functions $\Phi_{z,ox}(\lambda)$ were normalized to disregard any scaling $\Phi'_{z,ox}(\lambda)=\Phi_{z,ox}(\lambda)/\|\Phi_{z,ox}\|_2$. The tissue depth of 1 cm was selected for relating the application to small animal optoacoustic imaging.

The computed vectors $\Phi'_{z,ox}(\lambda)$ are used in the following as training data in the context of PCA to derive a linear model of Eigenspectra (a mean spectrum $\Phi_M(\lambda)$ and three Eigenspectra $\Phi_1(\lambda), \Phi_2(\lambda), \Phi_3(\lambda)$) as exemplarily shown in FIG. 2(a)-(d).

PCA captures the dominant variations of all spectral patterns used in the training dataset in the few first coefficients with a minimum mean square error. A model dimension of 3 Eigenspectra was selected for providing a rather simple model with a small associated error (see FIG. 2(e)).

Regarding the parameters $m_1$, $m_2$ and $m_3$ of the model on the training data set (see FIG. 2(f)-(h), respectively), it was surprisingly found that the values of $m_2$ can be greatly associated with tissue depth, while the values of $m_1$ can be greatly associated with the average levels of background tissue oxygenation. This indicates that the second Eigenspectrum $\Phi_2(\lambda)$ is mainly associated with the modifications of optical fluence due to depth and the average optical properties of the surrounding tissue, while the first Eigenspectrum $\Phi_1(\lambda)$ is associated with the "spectral shape" of optical fluence that relates to the average oxygenation of the surrounding tissue. Moreover, the highest and lowest values of these parameters on the training dataset can offer an indication of their limits $[\lim^{min}_i, \lim^{max}_i]$ expected in tissue.

A validation of the accuracy of the Eigenspectrum Model $(\Phi_M(\lambda), \Phi_1(\lambda), \ldots, \Phi_P(\lambda))$ over simulation-based optical fluence spectra created in arbitrary tissues yielded a very small model error, supporting the inventive approach according to which a simple linear model with only a few, e.g. three, Eigenspectra can capture the spectral variability of $\Phi'(r,\lambda)$ in complex tissue structures, independently of the optical properties, depth and blood oxygenation.

Similarly, the validity and accuracy of the Eigenspectrum model to capture optical fluence spectral patterns present in tissue was experimentally investigated by means of measurements from small animals in vivo and ex vivo, wherein the optical fluence in tissue was measured by inserting a reference chromophore with well characterized spectrum in deep tissue. The result of this investigation yielded that the Eigenspectrum model can capture realistically the spectral variability of optical fluence in tissue, even in the case of noisy experimental data obtained in vivo.

Inversion

Given the Eigenspectrum model for the optical fluence, the quantitative estimation of blood $sO_2$ using MSOT reduces to solving Eq. (3) using a non-linear optimization approach. Inversion can be performed independently for a single pixel in the image or simultaneously for a grid of pixels distributed appropriately in the image domain. In the second case additional constraints on the values of the Eigenspectrum model parameters can be imposed, based on the spatial and spectral characteristics of optical fluence.

In the following, three different inversion approaches are presented, namely (1) a per-pixel inversion using local or global optimization, (2) a constrained optimization on a grid of points, where the spatial characteristics of the optical fluence are further modelled, and (3) another constrained optimization, wherein both spatial and spectral characteristics of the optical fluence are taken into account for enhancing inversion stability.

(1) Single Pixel Inversion

In the single pixel inversion case, the optimization problem for a specific point r formulates as the minimization of the function in Eq. (5) over the values of $m_1^r$, $m_2^r$, $m_3^r$, $c'_{HbO2}(r)$ and $c'_{HHb}(r)$, constrained according to Eq. (6).

$$f = \left\| P(r,\lambda) - \left(\Phi_M(\lambda) + \sum_{i=1}^{P} m_i^r \Phi_i(\lambda)\right) \cdot \right.$$
$$\left. (c'_{HbO2}(r) \cdot \varepsilon_{HbO2}(\lambda) + c'_{HHb}(r) \cdot \varepsilon_{HHb}(\lambda)) \right\|_2 \quad (5)$$

$$lim_i^{min} < m_i^r < lim_i^{max}, \quad (6)$$
$$c'_{HbO2}(x) \geq 0,$$
$$c'_{HHb}(x) \geq 0.$$

Using a constrained local optimization algorithm to solve the non-linear optimization problem of Eq. (5) and (6) in the case of a simulated data set it can be observed that the problem is non-convex and thus the inversion converges accurately for only a small percentage of pixels. Accordingly, the optimization problem is a so-called ill-posed problem. Preferably, in order to further improve the accuracy of the inversion and to achieve a unique solution, further constraints are imposed on the values of the fluence parameters $m_i^r$.

(2) Inversion on a Grid of Points Incorporating Spatial Fluence Characteristics

Preferably, the spatial characteristics of optical fluence are further exploited for overcoming the ill-posed nature of the optimization problem. In contrary to tissue absorption which can vary arbitrarily, the optical fluence is bound to vary smoothly in space due to the nature of diffuse light propagation.

According to a preferred aspect of the Eigenspectrum model inversion, such a priori information is incorporated by attempting simultaneous inversion on a grid of points in the image domain, and penalizing large variation of the fluence model parameters $m_1^r$, $m_2^r$ and $m_3^r$ between neighbor pixels. This is preferably achieved through incorporation of appropriate Lagrange multipliers $\lambda_i$ to the non-linear inversion function for constraining the variation of one or all model parameters. The values of the Lagrange multipliers can be optimized using cross-validation on simulated data sets. Additionally, since the second Eigenspectrum is strongly associated with depth, the $m_2$ model parameter can be constrained to take lower values as tissue depth increases (in accordance with FIG. 2(g)).

FIG. 3 illustrates the incorporation of constraints on the spatial characteristics of fluence parameters $m_1^r$, $m_2^r$ and $m_3^r$, in the case of simultaneous inversion on a grid of points, wherein a directed graph on the grid of points enforces a constraint on the values of $m_2$ model parameter with depth (see FIG. 3(a)) and a non-directed graph on the grid of points penalizes great variations of the fluence parameters between neighbor points (see FIG. 3(b)).

Assuming a circular grid of P arcs and L radial lines (see FIG. 3) with a total of P×L points $r_{p,l}$, and let the vector $m_i = [m_i^{r1,1}, m_i^{r1,2}, \ldots, m_i^{r1,L}, m_i^{r2,1}, \ldots, m_i^{rp,l}, \ldots, m_i^{rP,L}]$ correspond to the values of the optical fluence parameter i (i=1 . . . 3) over all such points, the new inverse problem is preferably defined as the minimization of function $f_{grid}$ defined in Eq. (7) under the constraints defined in Eq. (8).

$$f_{grid} = \sum_i f(r_i) + \lambda_1 \|Wm_1\|_2 + \lambda_2 \|Wm_2\|_2 + \lambda_3 \|Wm_3\|_2 \quad (7)$$

$$lim_i^{min} < m_i^{r_k} < lim_i^{max}, \forall i, \forall k, \quad (8)$$
$$m_2^{r_{p+1,1}} < m_2^{r_{p,l}}, m_2^{r_{p+1,l+1}} < m_2^{r_{p,l}}, m_2^{r_{p+1,l-1}} < m_2^{r_{p,l}}$$
$$c_{HbO2}(r_k) \geq 0, \forall k,$$
$$c_{HHb}(r_k) \geq 0, \forall k.$$

In Eq. (7), W is the weighted connectivity matrix corresponding to grid of points assumed. Each matrix element corresponds to a pair of grid points $r_{p1,l1}$ $r_{p2,l2}$ and is zero if the points are not directly connected or inverse proportional to their distance ($w(r_{p1,l1}\, r_{p2,l2}) \propto 1/\|r_{p1,l1} - r_{p2,l2}\|$) if the points are connected.

Simultaneous inversion in a grid of points has surprisingly turned out to significantly enhance inversion stability.

(3) Inversion on a Grid of Points Incorporating Spatio-Spectral Fluence Characteristics For further enhancing the inversion stability, additional constraints can be imposed to the values of fluence parameters based on prior experimental measurements of the optical fluence in similar conditions or based on alternative prior knowledge that can be derived directly from the reconstructed multispectral optoacoustic images. Two possible examples of enforcing such constraints in the context of the grid inversion are described in the following:

Global Constraints on $m_1$

For instance, in certain cases of in vivo imaging, it can be preferably assumed that the average tissue oxygenation is higher than 50%, and thus the model parameter $m_1$ will obtain values lower or equal to zero as indicated by FIG. 2(f). This preferred assumption has been verified by multiple controlled in vivo experiments (where the animal is breathing 100% $O_2$ gas and imaging is performed in the brain or in the abdomen), where the measured fluence parameter $m_1$ was repeatedly found negative. Under this condition, and by constraining the values of $m_1^r$ to be negative in all grid points excellent convergence rate can be achieved also in the case of high levels superimposed noise. It is noted that no assumptions are made on the specific oxygenation values of the grid points, but only on the average tissue oxygenation.

Local Constraints on the Model Parameters

Alternatively, if no prior fluence measurements are available some constraints for the model parameter $m_1$ can be extracted from the available data themselves. By performing a first linear unmixing approach on the data a first estimation map of $sO_2$ levels can be obtained. It is noted that this $sO_2$ map is incrementally erroneous with tissue depth, however it can serve as a first approximation.

Using this $sO_2$ map and average tissue optical properties (e.g. $\mu_a=0.2$ cm$^{-1}$ at 800 nm and $\mu_s=10$ cm$^{-1}$) the optical fluence within tissue can be simulated and a first estimate on the values of one or all model parameters $m_1^r$, $m_2^r$ and $m_3^r$ (i.e. $\hat{m}_1^r$, $\hat{m}_2^r$, $\hat{m}_3^r$) can be extracted, where r corresponds to the positions of the grid points. In the following, the optimization problem of Eq. (7) to (8) is solved, with the only difference that the values of one or all of the model parameters $m_1^r$, $m_2^r$ and $m_3^r$ are constrained to lie in a region close to the initial estimates $\hat{m}_1^r$, $\hat{m}_2^r$, $\hat{m}_3^r$. It is noted that these regions need to be incrementally larger with depth since in deep tissue the original estimates deviate usually from the true values. Such an optimization approach incorporating prior information for the model parameters corresponding to each grid pixel can also be formulated in the context of Bayesian inversion. By constraining the problem in such a way the inversion stability is also greatly enhanced also in cases of high random noise.

FIG. 4 relates to an example of an inversion of Eq. (7) and (8) on a grid of 64 points in the case of a simulated dataset and shows the error in the estimation of local blood $sO_2$ for all grid points when using the inventive method (blue curve) and when using simple linear non-negatively constrained unmixing (red curve). As apparent from the comparison, the inventive method is associated with a very small error in the estimation of blood oxygenation as compared to linear unmixing which is frequently used as an approximation.

Application on Tissue Images

In the following, the inventive Eigenspectrum method is exemplarily demonstrated in the case of experimental MSOT data. A nude mouse bearing an orthotopic Mammarian 4T1 tumor was imaged in the tumor area in eight excitation wavelengths from 690 nm to 900 nm.

FIG. 5(a) depicts the anatomical optoacoustic image acquired at wavelength 900 nm. The points on the image correspond to the initial grid of pixels that were selected for the application of the non-linear inversion scheme described above. The grid was selected to cover the tumor area. The grid of pixels is in the following automatically adjusted to avoid using pixels of low image intensity (and thus low SNR) in the inversion.

After applying the non-linear inversion scheme on the refined grid of points (see FIG. 5(b)), estimates for fluence parameters $m_1^r$, $m_2^r$ and $m_3^r$ are obtained for each grid point r. In the following, the fluence parameters for each pixel in the convex hull of the grid is obtained using cubic interpolation, thus resulting in fluence maps for the image sub-region.

FIG. 5(c) presents such a map for fluence parameter $m_2$. The wavelength dependence of optical fluence is computed for each pixel within these maps as in $\Phi'(r,\lambda)=\Phi_M(\lambda)+m_1^r\Phi_1(\lambda)+m_2^r\Phi_2(\lambda)+m_3^r\Phi_3(\lambda)$, where $\Phi_i(\lambda)$ is the ith fluence Eigenspectrum.

Finally, a fluence-corrected MSOT image is obtained after diving the original image $P(r,\lambda)$ with the normalized wavelength dependent optical fluence $\Phi'(r,\lambda)$ at each position r and wavelength $\lambda$: $P^{corr}(r,\lambda)=P(r,\lambda)/\Phi'(r,\lambda)$. After fluence correction, non-negatively constrained linear spectral unmixing with the spectra of oxy and deoxy-hemoglobin can result in an estimation of tissue blood oxygenation.

FIG. 5(d) presents the estimated tissue oxygenation in the area of the tumor as computed using the Eigenspectrum method. Tissue oxygenation is overlaid to the anatomical image with pseudocolor, represented in gray scale.

Figure 6:
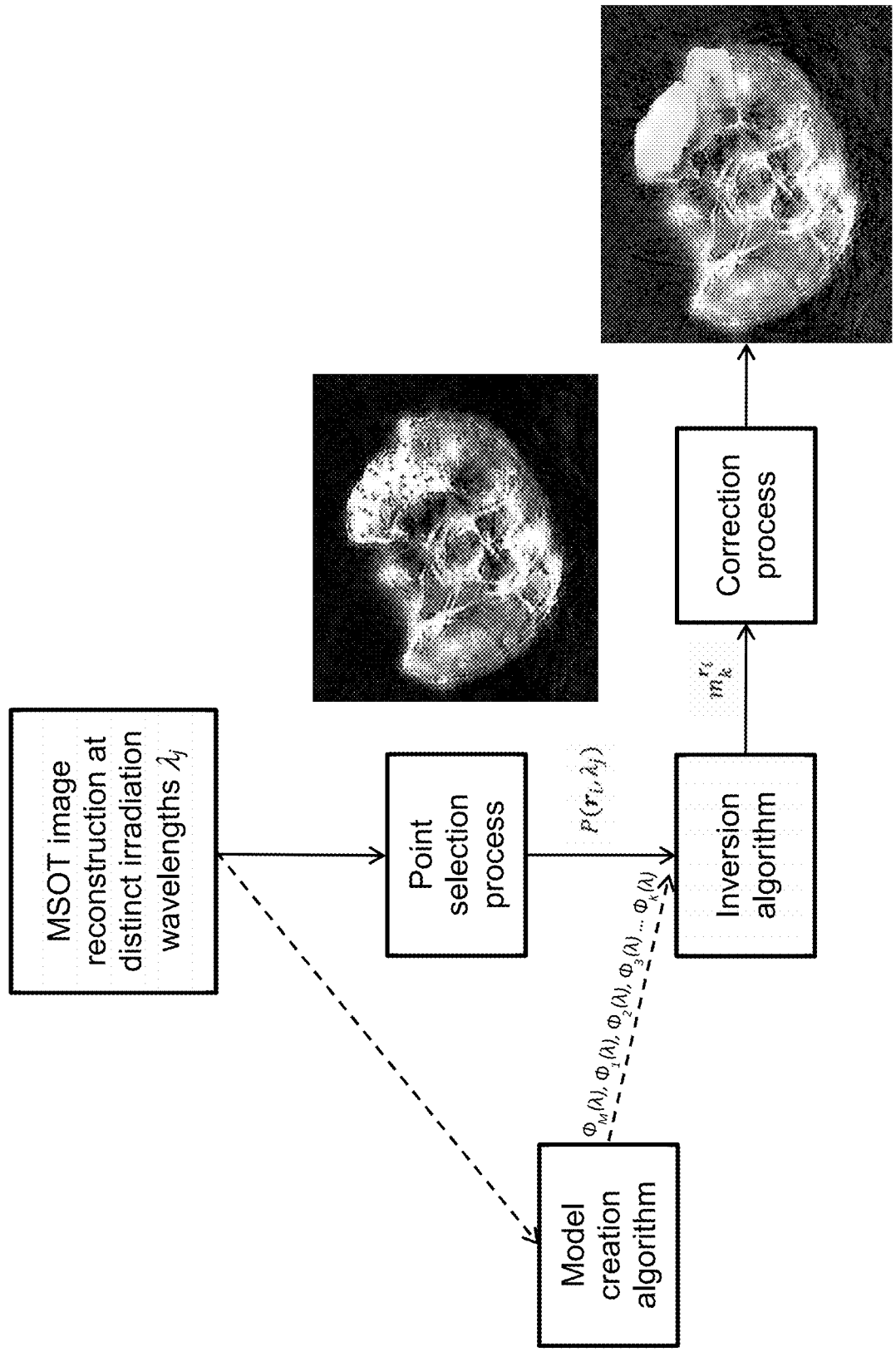

FIG. 6 shows an overview on an example of processes and algorithms of a method for multispectral optoacoustic imaging. In present example, oxygenated ($HbO_2$) and deoxygenated (HHb) hemoglobin being the main tissue absorbers in the object 1.

In a first step, MSOT images are reconstructed at distinct irradiation wavelengths $\lambda_j$ based on detected acoustic waves which are generated in the object 1 (see FIG. 1) upon irradiating the object 1 with transient electromagnetic radiation at the irradiation wavelengths $\lambda_j$.

In a second step, the reconstructed MSOT images undergo a point selection process, wherein reliable pixels $r_i$ in the image domain are selected in a semiautomatic way or by user annotation.

Optoacoustic image intensities $P(r_i,\lambda_j)$ at the selected pixels $r_i$ for all irradiation wavelengths $\lambda_j$ are processed in a third step, wherein fluence parameters $m_k^{r_i}$ and concentration values, e.g. $sO_2$ values, are computed for each pixel $r_i$ in the grid using the image intensities $P(r_i,\lambda_j)$ and a pre-determined model of the fluence in the object, wherein the model is based on a linear combination of model spectra $\Phi_k(\lambda)$. This is performed by means of an inversion algorithm solving the following equation:

$$P(r_1, \lambda_1) = \left(\Phi_M(\lambda_1) + \sum_{k=1}^{K} m_k^{r_i}\Phi_k(\lambda_1)\right)$$
$$(c'_{HbO2}(r_1)\varepsilon_{HbO2}(\lambda_1) + c'_{HHb}(r_1)\varepsilon_{HHb}(\lambda_1))$$

$$P(r_1, \lambda_2) = \left(\Phi_M(\lambda_2) + \sum_{k=1}^{K} m_k^{r_i}\Phi_k(\lambda_2)\right)$$
$$(c'_{HbO2}(r_1)\varepsilon_{HbO2}(\lambda_2) + c'_{HHb}(r_1)\varepsilon_{HHb}(\lambda_2))$$

...

$$P(r_1, \lambda_{Nw}) =$$
$$\left(\Phi_M(\lambda_{Nw}) + \sum_{k=1}^{K} m_k^{r_i}\Phi_k(\lambda_{Nw})\right)(c'_{HbO2}(r_1)\varepsilon_{HbO2}(\lambda_{Nw}) + c'_{HHb}(r_1)\varepsilon_{HHb}(\lambda_{Nw}))$$

The calculated fluence parameters $m_k^{r_i}$ (i=1 to Np, Np being the number of selected pixels, k=1 to K, K being the number of model spectra) can be used to infer the wavelength dependence of the optical fluence in the whole area corresponding to the convex hull of the grid by means of interpolation, i.e. the $m_k$ values are interpolated from $m_k^{r_i}$ for all intermediate pixels in the convex hull of the grid of points.

Subsequently, the wavelength dependence of the optical fluence is computed for each pixel within the convex hull as in $\Phi'(r,\lambda)=\Phi_M(\lambda)+m_1^r\Phi_1(\lambda)+m_2^r\Phi_2(\lambda)+m_3^r\Phi_3(\lambda)+\ldots$.

A fluence-corrected MSOT image is obtained after dividing the originally reconstructed MSOT image $P(r,\lambda)$ with the normalized wavelength-dependent optical fluence $\Phi'(r,\lambda)$ at each position r and wavelength $\lambda$: $P^{corr}(r,\lambda)=P(r,\lambda)/\Phi'(r,\lambda)$.

After fluence correction, non-negatively constrained spectral unmixing within the spectra of oxy- and deoxyhemoglobin result in the determination of a particularly accurate $sO_2$ map.

Preferably, the model of the fluence, in particular the model spectra $\Phi_k(\lambda)$, is established independently, in particular in advance, of the current measurements by means of a model creation algorithm, wherein base functions of the wavelength dependence of the optical fluence in the object are created for the excitation wavelengths $\lambda_j$ employed. Preferably, in distinction to previous fluence modeling methods, only the wavelength dependence of optical fluence is modeled but not the actual fluence in absolute terms. Moreover, modeling is performed by applying a statistical procedure on training data and not via a spatial light propagation model that is fitted to the MSOT images.

SUMMARY

The invention relates to a novel solution for the problem of quantitative multispectral optoacoustic imaging of tissue oxygenation. According to preferred aspects of the invention, a simple linear model for successfully capturing the spectral variability of optical fluence with wavelength in tissue was created and validated. Using this model, a non-linear inversion scheme for correcting for the optical fluence and obtaining accurate quantitative estimates of tissue blood oxygenation was formulated. Formulating the quantification problem of MSOT as a per-pixel non-linear unmixing problem instead of a model-based optical property estimation approach allows for greater flexibility and easier applicability in experimental images of tissue. The inventive methodology does not assume full and accurate spatial information, and does not rely on absolute image values that are prone to error due a multitude of phenomena that are often not modelled in image reconstruction (e.g. spatial sensitivity field of the ultrasound arrays, ultrasound attenuation and scattering, Grüneisen coefficient). In this respect the inventive method is readily applicable in in vivo MSOT images. Furthermore, since the presented inverse problem is of low dimensionality (typically 300-500 unknown parameters for the case of grid inversion), the computational cost is rather low. Specifically, the required computational time for the inversion of a grid of 64 points using an Intel Core i7-4820K can be less than 1 minute.

Based on a validation of the inventive approach, a rather simple 3-dimensional model has turned out sufficient for accurately capturing the spectral variability of optical fluence, independently of the optical properties and the physiology of the surrounding tissue.

Basically, the absorption of water, lipids and melanin also present in tissue may be ignored under an appropriate wavelength selection, assuming that the influence of hemoglobin is much more prevalent in the near-infrared region. Moreover, the wavelength dependence of scattering may be ignored. However, according to preferred embodiments of the invention, the influence of such parameters could also be incorporated similarly for optimizing the Eigenspectrum model.

Despite the aforementioned simplifying assumptions, a model fit in the case of in vivo and ex vivo experimental optoacoustic images of mice indicated a very promising match between theory and experimental reality.

Because the inverse problem, in its simplest form (per pixel inversion), is non-convex and ill-posed, in a per pixel inversion case different combinations of optical fluence and local oxygenation may produce an almost identical result after multiplication. Thus, the nonlinear inversion may converge to a wrong solution unless additional restrictions are applied.

Therefore, it is particularly preferred to incorporate spatio-spectral fluence characteristics using available prior knowledge into a more complex inversion scheme. In this way, inversion stability was achieved even in cases where the spectra are corrupted by random noise. The preferred inversion scheme provides accurate estimates of tissue oxygenation with far lower estimation error than the one of linear spectral un-mixing, that is typically used today in experimental studies as an approximation.

What is claimed is:
1. A device for multispectral optoacoustic imaging of an object, the device comprising:
  a) an irradiation unit comprising at least one laser source configured to emit electromagnetic radiation including visible and/or near-infrared light, the irradiation unit configured to irradiate the object with the electromagnetic radiation at two or more different irradiation wavelengths, said electromagnetic radiation having a time-varying intensity;
  b) a detection unit comprising one or more ultrasound detectors, the detection unit configured to detect acoustic waves generated in the object upon irradiating the object with the electromagnetic radiation at the different irradiation wavelengths, wherein at least one electromagnetic radiation absorber in the object absorbs the electromagnetic radiation; and
  c) a processor configured to:
    reconstruct images of the object based on the detected acoustic waves generated in the object at each of the different irradiation wavelengths; and
    determine a spatial distribution of at least one first concentration value, which relates to a concentration of the at least one electromagnetic radiation absorber in the object,
  wherein the determination of the spatial distribution of the at least one first concentration value is based on the reconstructed images at the different irradiation wavelengths, at least one wavelength-dependent extinction coefficient of the at least one electromagnetic radiation absorber in the object, and a linear combination of at least two model spectra, the model spectra representing wavelength-dependent basis functions of a radiation fluence or wavelength-dependent basis functions of a normalized radiation fluence.

2. The device according to claim 1, wherein the processor is configured to determine spatial distributions of at least two first concentration values relating to concentrations of at least two electromagnetic radiation absorbers in the object, wherein the determination of the spatial distributions of the at least two first concentration values is based on the reconstructed images at the different irradiation wavelengths, the wavelength-dependent extinction coefficients of the at least two electromagnetic radiation absorbers in the object, and the linear combination of the at least two model spectra, and to derive a spatial distribution of a second concentration value from the determined spatial distributions of the at least two first concentration values.

3. The device according to claim 2, wherein the second concentration value relates to blood oxygenation saturation in a biological tissue.

4. The device according to claim 1, wherein the at least two model spectra have been determined by
  determining a set of spectral patterns for different depths in a medium and for different concentrations of the at least one electromagnetic radiation absorber in the medium, and
  applying a statistical procedure on the set of spectral patterns.

5. The device according to claim 4, the set of spectral patterns having been obtained from:
  analytical solutions or numerical solutions of a diffusion equation or a radiative transfer equation for the different irradiation wavelengths, Monte Carlo simulations of light propagation for the different irradiation wavelengths, and/or a set of experimental measurements for the different irradiation wavelengths.

6. The device according to claim 4, the statistical procedure applied on the set of spectral patterns comprising:

a principal component analysis;

a kernel principal component analysis; and/or a linear discriminant analysis.

7. The device according to claim 1, the linear combination of the model spectra corresponding to an addition of a mean model spectrum and a linear combination of a first number of further model spectra, wherein each of the further model spectra is multiplied by a model parameter.

8. The device according to claim 7, the irradiation unit being configured to irradiate the object with the electromagnetic radiation at a second number of the different irradiation wavelengths, wherein the second number is larger than or equal to the sum of the first number of further model spectra and a number of the first concentration values to be determined.

9. The device according to claim 1, further comprising a second electromagnetic radiation absorber in the object for absorbing the electromagnetic radiation such that there are two different electromagnetic radiation absorbers in the object and further comprising another first concentration value such that there are two first concentration values, wherein the determination of the spatial distribution of the two first concentration values, which relate to concentrations of the two different electromagnetic radiation absorbers in the object, comprises an inversion of a system of non-linear equations, wherein the inversion of the system of non-linear equations is performed simultaneously for a selected set of different positions distributed in an image domain.

10. The device according to claim 1, further comprising a second electromagnetic radiation absorber in the object for absorbing the electromagnetic radiation such that there are two different electromagnetic radiation absorbers in the object another first concentration value such that there are two first concentration values; and a second wavelength-dependent extinction coefficient such that there are two wavelength-dependent extinction coefficients, wherein the determination of the spatial distribution of the two first concentration values, which relate to concentrations of the two different electromagnetic radiation absorbers in the object, comprises an inversion of a system of non-linear equations given by $$P(r, \lambda_j) = (\Phi_M(\lambda_j) + \Sigma^P_{i=1} m_i^r \Phi_i(\lambda_j))(C'_1(r)\varepsilon_1(\lambda_j) + c'_2(r)\varepsilon_2(\lambda_j)), \text{ with } j=1\ldots w,$$

$P(r, \lambda_j)$ denoting the intensity of a reconstructed image of the object at a position r and an irradiation wavelength $\lambda_j$;

$\Phi_M(\lambda_j) + \Sigma^P_{i=1} m_i^r \Phi_i(\lambda_j)$ denoting a linear combination of the wavelength-dependent model spectra $\Phi_M(\lambda)$ and $\Phi_i(\lambda)$, with i=1...p, at an irradiation wavelength $\lambda_j$, wherein $m_i^r$ denotes model parameters at the position r, and $c'_1(r)\varepsilon_1(\lambda_j) + c'_2(r)\varepsilon_2(\lambda_j)$ denotes a linear combination of the wavelength-dependent extinction coefficients $\varepsilon_1(\lambda_j)$ and $\varepsilon_2(\lambda_j)$ of the two electromagnetic radiation absorbers at an irradiation wavelength $\lambda_j$, wherein $c'_1(r)$ and $c'_2(r)$ denote the two first concentration values at the position r.

11. A method for multispectral optoacoustic imaging of an object, comprising the following steps:

a) irradiating the object with electromagnetic radiation at two or more different irradiation wavelengths, said electromagnetic radiation having a time-varying intensity;

b) detecting acoustic waves generated in the object upon irradiating the object with the electromagnetic radiation at the different irradiation wavelengths; and c) absorbing the electromagnetic radiation by at least one electromagnetic radiation absorber in the object;

d) reconstructing images of the object based on the detected acoustic waves generated in the object at each of the irradiation wavelengths; and e) providing instructions for execution by a processor that, when executed by the processor, cause the processor to determine a spatial distribution of at least one first concentration value, which relates to a concentration of the at least one electromagnetic radiation absorber in the object, wherein the determination of the spatial distribution of the at least one first concentration value is based on the reconstructed images at the different irradiation wavelengths, at least one wavelength-dependent extinction coefficient of the at least one electromagnetic radiation absorber in the object, and a linear combination of at least two model spectra, the model spectra representing wavelength-dependent basis functions of a radiation fluence or wavelength-dependent basis functions of a normalized radiation fluence.

* * * * *